United States Patent [19]

Bacus

[11] 4,266,505

[45] May 12, 1981

[54] APPARATUS FOR THE PREPARATION OF BLOOD SAMPLES FOR AUTOMATED ANALYSIS

[75] Inventor: James W. Bacus, Hinsdale, Ill.

[73] Assignee: Rush-Presbyterian-St. Luke Medical Center, Chicago, Ill.

[21] Appl. No.: 51,896

[22] Filed: Jun. 25, 1979

Related U.S. Application Data

[60] Division of Ser. No. 862,735, Dec. 21, 1977, Pat. No. 4,209,548, which is a continuation of Ser. No. 737,532, Nov. 1, 1976, abandoned.

[51] Int. Cl.³ .............................................. B44D 1/02
[52] U.S. Cl. ..................................... 118/699; 118/52; 118/64
[58] Field of Search ............... 118/52, 699, 64; 424/3; 427/2

[56] References Cited

U.S. PATENT DOCUMENTS

| | | | |
|---|---|---|---|
| 3,352,280 | 11/1967 | Hughes | 118/31 |
| 3,705,048 | 12/1972 | Staunton | 427/2 |
| 3,870,789 | 3/1975 | Mikat | 424/3 |
| 4,037,003 | 7/1977 | Maher | 427/2 |

*Primary Examiner*—Sam Silverberg
*Attorney, Agent, or Firm*—Fitch, Even, Tabin, Flannery & Welsh

[57] ABSTRACT

An apparatus for preparing blood samples containing red blood cells for automated analysis wherein the blood sample on a slide is spun to create a monolayer of randomly distributed red blood cells. To inhibit cell morphology distortions from occurring during drying, the morphologies of the cells contained in the monolayer are preserved by a fixing agent after monolayer preparation but prior to drying when such distortions would otherwise develop. The method and apparatus are particularly useful for fixing red blood cells to prevent loss of or deformation of a central pallor which would be detrimental to a subsequent automated analysis.

2 Claims, 4 Drawing Figures

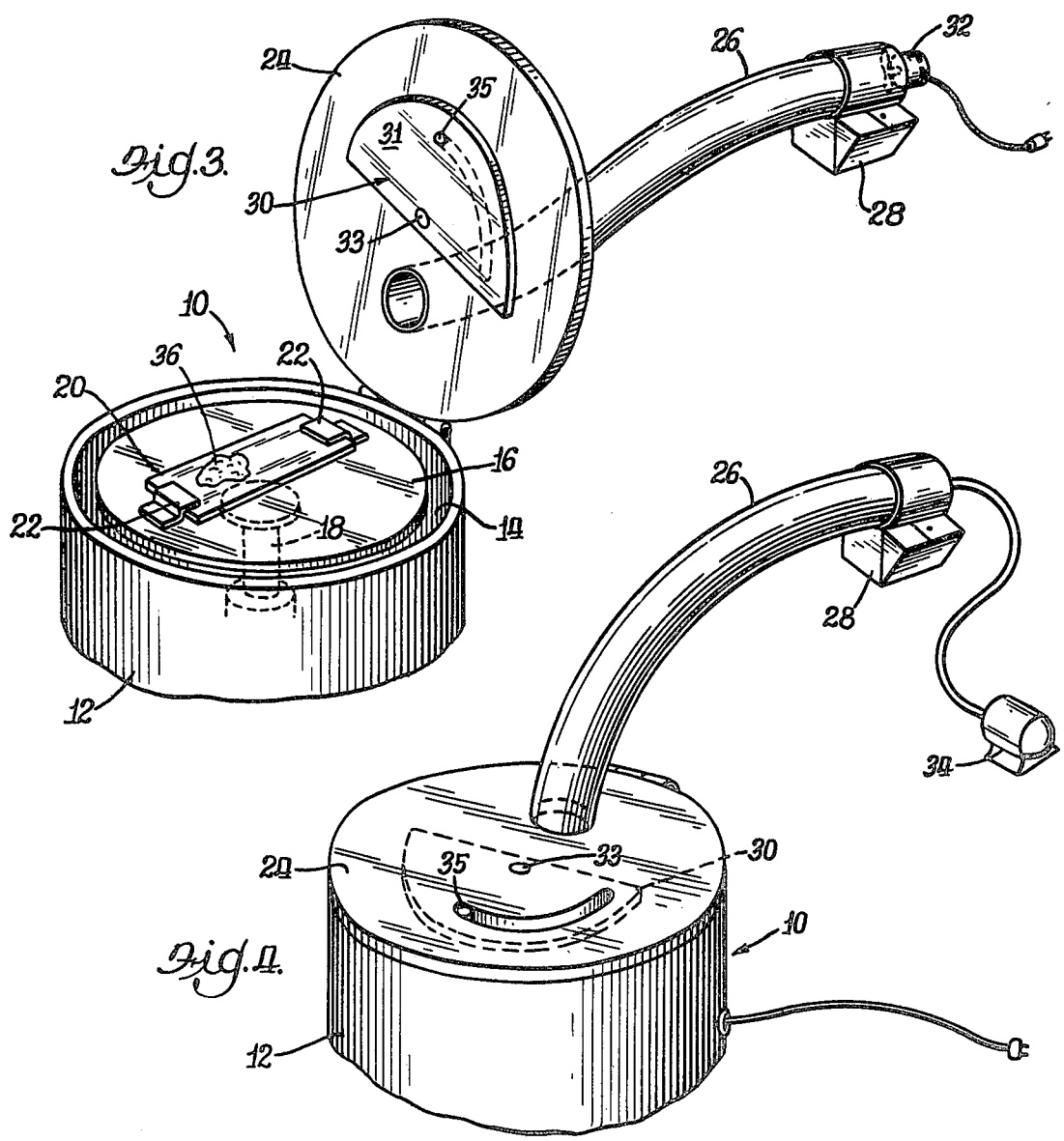

APPARATUS FOR THE PREPARATION OF BLOOD SAMPLES FOR AUTOMATED ANALYSIS

This is a division of application Ser. No. 862,735, filed Dec. 21, 1977, now U.S. Pat. No. 4,209,548, which is a continuation of Ser. No. 737,532 filed Nov. 1, 1976 abandoned.

This invention relates to a method of, and an apparatus for, the preparation of blood cell specimens for diagnostic analysis. More specifically, the invention is particularly directed to the fixing or preservation of the morphology of cells for later automated analysis.

The present invention is particularly directed to fixing cells during a precise and critical step of sample preparation, such that their morphology is preserved for later analysis. Thus, the development of distortions encountered by other known methods of sample preparation having cells on a slide is reduced to a minimum. Although the present invention is not to be construed as limited to any particular kind of cell or sample, it will be described in connection with the preparation of red blood cells for automatic analysis on a rapid basis. One distortion noted heretofore in known methods of preparation of microscopic slides was that of the alteration of morphology of certain red blood cells, particularly the loss by certain cells of their central pallor, i.e., a thin central indented region in a cell, with the cell becoming more rounded and resembling spherocytes or other cells of a similar diameter or shape.

The diagnosis of various kinds of anemia is enhanced by accurate analysis of the sizes of the red blood cells and the quantification of red cell parameters, such as the Wintrobe indices of mean cell volume, mean cell hemoglobin and mean cell hemoglobin concentration. At the present time, such information is typically acquired by the use of a Coulter Counter which measures the number of red blood cells per cubic millimeter, the hemoglobin concentration, and the mean cell volume in a liquid flow system. In addition to this information provided by the Coulter Counter, it would be most helpful to have an accurate analysis of the kinds of cells present in the sample in accordance with established hematological classifications, such as normocytes, macrocytes, target cells, microcytes, spiculed cells, hypochromic elongated cells, spherocytes, etc. A method of and apparatus for classifying individual cells into such classifications, i.e., subpopulations, and providing red blood cell parameters for each of the subpopulations, is disclosed in co-pending application of James W. Bacus, entitled "A Method of and an Apparatus for Automatic Classification of Red Blood Cells", filed on even date, this application being incorporated by reference as if fully reproduced herein.

The oldest and most common method of preparing microscopic slides for a manual evaluation under a microscope involves the wedge-slide technique in which a quantity of blood on a glass slide is wiped by a second slide along the surface of the first slide to produce a thin blood layer on the first slide. After the layer dries, which requires only a short time, the slide is dipped into a staining agent and then the operator views the slide under a microscope and visually analyzes the red cell population. In addition to being time consuming, the physical action of the wiping slide tends to distort the morphology of many of the cells. Typically, under the best of conditions, only a fraction of the surface area of the slide is suitable for analysis. This distortion renders this wedge technique unsuitable for automated red blood cell analysis.

There has been developed, particularly for white blood cell analysis, a spinning technique for the formation of a monolayer of cells on a slide for later automated analysis of the white blood cells. Essentially, such an apparatus spins a slide and the blood placed thereon in the plane of the surface on which the blood rests with the excess blood being hurled outwardly from the slide surface. Surface tension and/or other forces retain a monolayer of blood upon the slide. For white blood cell work, the cells in the monolayer are allowed to dry and then are stained with a Wright's stain (or other stain) and analyzed automatically such as disclosed in U.S. Pat. No. 3,883,852.

While the drying of the white blood cells has not produced a substantial distortion from a white blood cell analysis standpoint, it has been found that the drying of the red blood cells produces undesirable types of distortions, particularly a loss of central pallor for many of the red blood cells as they dry. It is not entirely clear what causes these shape changes, but they apparently are caused by surface tension, charges and/or drying effects.

The spinning technique causes the preferred monolayer of red blood cells to be formed on the slide with the red blood cells separated, that is, spaced from each other. Should such a slide be dipped into a fixing or staining liquid before the cells are dry, the red blood cells would be washed from the slide. If the red blood cells are fixed in solution, prior to deposition on the slide, the fixation causes them to cluster together such that a monolayer of separated cells is not obtained. Thus, it is desirable to fix the cells during the period after monolayer formation, but prior to drying.

Accordingly, a general object of the invention is to provide a method for fixing cell morphology of cells on a slide after the monolayer formation, but prior to the drying of the cells on the slide to preserve their identifying features for later analysis.

Other objects and advantages of the invention will become apparent from the detailed description taken in connnection with the accompanying drawings in which:

FIG. 1 is an enlarged diagrammatic top view of a microscope slide with a monolayer of red blood cells having central pallors and a red blood cell lacking a central pallor;

FIG. 2 is a side elevational view of the slide and cells shown in FIG. 1;

FIG. 3 is a perspective view of an apparatus, in an open position, embodying various features of the invention; and FIG. 4 is a perspective view of an apparatus, in a closed position, embodying various features of the invention.

Generally, in accordance with the method of the present invention, a quantity of blood sample is placed upon a microscope slide which is then spun by a centrifugal spinner. The spinning action of the slide throws all but a monolayer of the blood from the slide. Before the sample has dried to the extent that red cells would normally be distorted by such drying, a suitable fixing agent is applied to the monolayer to preserve the shapes of the red cells so that further drying does not adversely change the cell morphology to the extent of losing the central pallor configurations.

Referring to FIG. 3, an apparatus for practicing the disclosed method comprises a centrifugal spinner 10 including a housing 12 defining a top-opening interior chamber 14 within which there is disposed a platen 16 rotatably mounted on the end of a shaft 18. The platen receives a slide 20 on the upper horizontal flat surface of the platen for spinning of the slide in a horizontal plane. The slide 20 is releasably held in position on the platen by appropriate means 22 such as lugs or the like that are spaced apart on the platen surface to receive the slide. The shaft 18 is driven by motor means (not shown) with the rate and duration of spinning being controlled by conventional means well known in the art. Suitable spinners are commercially available, and may be of the kind shown in U.S. Pat. Nos. 3,853,092 and 3,906,890.

In accordance with one embodiment of the disclosed invention, the top opening of the chamber of the spinner is closable as by a covering hood 24 adapted to rest on the housing 12 in position over the top opening. In the depicted embodiment, the hood 24 is connected in communication, as by a conduit 26, with a source of vaporous fixing agent, such as a canister 28 containing the fixing agent. A valve means 30 interposed in the conduit 26 intermediate its opposite ends provides control over the flow of vapor between the source and the interior chamber 14 of the spinner. Herein, the valve 30 comprises a semi-circular valve plate 31 pivoted at the center by a pin 33 fixed on the cover hood. The valve plate is pivoted to cover or uncover the discharge orifice of the conduit 26 when an upstanding handle pin 35 is gripped and swung in an arc. To the end of urging the flow of vapor to the chamber, the pressure within the canister is maintained at a higher level than the pressure within the spinner chamber, such as by a fan 32 mounted within the canister 28 or by an air pump 34 supplying air to the canister.

As noted above, in preparing a blood sample for analysis, a quantity of the blood sample 36 is placed upon the slide 20 which is then mounted upon the spinner platen 16 disposed within the chamber 14. The slide is spun at a rate and for a period of time necessary to develop an evenly distributed monolayer of red blood cells upon the surface of the slide. Commonly, the spinning rate is held constant, at a rate between 4,000 and 10,000 rpm with the actual period of spinning being relatively short, e.g., less than one second to 2.5 seconds, as is required to develop a satisfactory monolayer.

As disclosed in an article by James W. Bacus, "Erythrocyte Morphology and Centrifugal 'Spinner' Blood Film Preparations", *The Journal of Histochemistry and Cytochemistry*, 22:7:506–516, 1974, the blood samples are preferably diluted to adjust their plasma viscosities such that the sample may be spun for constant spin time and at a constant speed to provide the monolayer of cells having good separation and central pallor development. By way of example, a thoroughly mixed sample of whole blood was diluted with a serum albumin solution of 1.3 relative viscosity to adjust the hematocrit of each sample to 18%. The viscosity was relative to $H_2O$ as 1.0 and a typical range of relative viscosities for blood plasma is 1.2–1.8. Alternatively, a standard isotonic saline solution in a convenient ratio, e.g., 1:1, may be used as a diluent for most bloods. As is recognized in the art, if the spinning period is too short, the cells are clustered together and thus impossible to isolate and classify individually. If the spinning period is too long, there is an undue distortion of the cell shapes.

Rather than adjusting the plasma viscosity and using a constant spin time, as preferred, spin apparatus may be used which controls the spinning period. One of these is disclosed in U.S. Pat. No. 3,827,805 and employs a light beam which passes through the slide and sample during spinning. By measuring the degree of scattering of the beam caused by the blood cells, spinning may be stopped when a predetermined cell distribution is achieved. Another apparatus for controlling the spinning period is disclosed in U.S. Pat. No. 3,906,890. Using this apparatus, the operator determines the approximate blood cell concentration of the sample and sets the spinning time in accordance therewith. The present invention may be used with either of these patented apparatuses, but is not limited to either such apparatus.

Desirably, the monolayer of red blood cells on the slide is fixed and dried to the degree that permits mechanical handling of the slide without disruption or dislocation of the cells. Typically, a monolayer of blood on a slide air dries within 10 to 15 seconds after spinning is stopped, the time varying with humidity and other conditions. Heretofore, drying of the monolayer, as noted above, resulted in deleterious distortion of the red blood cells with resultant lack of identification of cells with central pallor and false identification of the misshapen cells. By way of example, red blood cells 40 and 42 are illustrated in solid lines in FIG. 1 as having a central pallor area 44, which is fixed by a fixing agent indicated by arrows in FIG. 2, to fix the central pallor against the loss thereof during a subsequent drying of the cells. Without fixing the cells 40 and 42 prior to drying, the cells flatten and assume the flattened shapes 40a and 42a, as shown in dotted lines in FIG. 2. The flatten cells 42a and 40a having a lost or severely distorted central pallor region are found to be difficult to distinguish from a true spherocyte cell 46, which never had a central pallor, as seen in FIG. 1, by automated analysis equipment.

In accordance with the disclosed method, it has been found that the red blood cells can be dried adequately without alteration of the cell morphology by fixing the red blood cells during the course of or immediately after the spinning, when the cells have attained a monolayer status with proper dispersion of the cells, but prior to the time when the drying process has progressed to the extent that the cell morphology is unacceptably altered. Such fixation has been found to set the physical geometry of the cells whereby the drying of the monolayer can proceed without the cell distortion noted in the prior art. In a preferred embodiment, the fixation step is performed when the monolayer has been established and the spinning force has been removed, so that the fixation occurs before too much drying has occurred. This is accomplished in accordance with the present disclosure by introducing into the chamber in which the slide is spun a fixing agent that is in the form of a vapor, so that its presence causes no ill effect upon the blood sample. This fixation step substantially sets the cell morphology.

Fixing of the cells prior to spinning has been found to prevent the dispersion of the cells in the desired monolayer, resulting rather in clumping or stringing of the cells when they subsequently are spun. Also, the introduction of a liquid fixing agent onto the slide, after spinning, but before drying, has been found to disrupt the cell dispersion, even to the point of washing the blood sample from the spinning slide.

One fixing agent which has proven effective is formaldehyde, a gas at normal room temperatures. In the depicted apparatus, formalin (an aqueous solution of between about 37% and 50% formaldehyde and about 15% methanol, by volume), is stored in the canister 28. The formaldehyde escapes from the solution and is conveyed to the chamber 14 of the spinner 10 by the conduit 26. Alternatively, the slide 20 with the monolayer of blood thereon can be quickly removed from the spinner chamber and placed in an atmosphere of vaporous formaldehyde. This latter step is less desirable in view of the relatively short time, i.e., about 5 seconds, available within which the transfer must be made if the fixation is to take effect before deleterious drying occurs. Further, the "closed" system in the depicted embodiment is preferred as an aid in controlling the vaporous formaldehyde which is toxic at levels greater than 5 ppm and creates a risk at concentrated levels. Exposure of the monolayer for about five minutes to an atmosphere of vaporous formaldehyde provides the desired fixation of the red blood cells.

When the blood sample is spun, the vast majority of the sample is spun from the slide to the interior walls of the spinner housing 12. This blood may contain a variety of harmful organisms, so that in some spinners, a liquid (usually water) is cascaded over the interior walls of the housing 12 during spinning to serve as a safety seal against escape of such organisms from the chamber. The flying blood is thus washed away through a drain in the bottom of the spinning compartment. One method of practicing the present invention includes replacing this cascading water with formalin. Thus, formaldehyde vapors are produced in the spinner from the time spinning commences. In this method, the spinning and establishment of a monolayer occurs sufficiently rapidly, i.e., within about 0.5 seconds, so that even though the vaporous formaldehyde is initially present in the spinning chamber, fixation does not occur until after the cells have been dispersed into the monolayer.

After the sample has been fixed and dried, the slide 20 is removed from the spinner or fixing chamber and analyzed by automated means. Red blood cells 40 and 42, fixed in the manner described herein, have been found to retain their characteristic central pallors 44 and other physical characteristics such that the samples so prepared provide a true and accurate indication of the morphology of the cells when analyzed using automated analyzers.

While a preferred fixing agent of formaldehyde has been used effectively, it is expected that other, methyl, ethyl or short-chain alcohols may be used in lieu of formaldehyde, or that other fixations, such as heating, for example, by microwaves, or other physical or chemical means may be used. Therefore, the present invention is not to be construed as limited to any particular fixing agent.

While a preferred embodiment has been shown and described, it will be understood that there is no intent to limit the invention by such disclosure, but rather, it is intended to cover all modifications and alternative constructions falling within the spirit and scope of the invention as defined in the appended claims.

What is claimed is:

1. In an apparatus for preparing a blood specimen in a monolayer of red blood cells on a slide suitable for automated analysis comprising housing means defining a spinning chamber, rotatable platen means disposed substantially horizontally within said chamber and adapted to receive slide means having deposited thereon a blood sample containing red blood cells, drive means adapted to rotate said platen means and to throw excess blood cells from said platen, means controlling the period of actuation of said drive means to dispose said red blood cells in substantially a monolayer on said slide and to stop rotation of said platen means after less than 2.5 seconds of rotation, means for generating a vaporous fixing agent at a location remote from said rotatable platen means, conduit means for introducing a vaporous fixing agent without wetting said cells to said red blood cells on said platen following their dispersal into substantially a monolayer on said slide to fix said cells in about fifteen minutes.

2. An apparatus in accordance with claim 1 wherein said means for generating a vaporous fixing agent generates the same at a first pressure that is higher than the pressure in said spinning chamber and a location exterior of said spinning chamber, said conduit means connecting said generating means to said spinning chamber including remote conduit external of said spinning chamber and valve means interposed in said conduit means and controlling the flow of vaporous fixing agent through said conduit means from a location exterior of said spinning chamber to a location within said spinning chamber.

* * * * *